(12) United States Patent
Schmitt et al.

(10) Patent No.: US 10,289,652 B2
(45) Date of Patent: *May 14, 2019

(54) CALIBRATION METHOD FOR THE PROSPECTIVE CALIBRATION OF MEASURING EQUIPMENT

(71) Applicant: Roche Diabetes Care, Inc., Indianapolis, IN (US)

(72) Inventors: Nikolaus Schmitt, Heidelberg (DE); Gerhard Frisch, Edingen-Neckarhausen (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 60 days.

This patent is subject to a terminal disclaimer.

(21) Appl. No.: 14/944,981

(22) Filed: Nov. 18, 2015

(65) Prior Publication Data

US 2016/0070675 A1    Mar. 10, 2016

Related U.S. Application Data

(63) Continuation of application No. 13/405,815, filed on Feb. 27, 2012, now Pat. No. 9,222,951, which is a (Continued)

(30) Foreign Application Priority Data

Aug. 27, 2009 (EP) .................... 09168797

(51) Int. Cl.
*A61B 5/00* (2006.01)
*A61B 5/145* (2006.01)
(Continued)

(52) U.S. Cl.
CPC ............ *G06F 17/18* (2013.01); *A61B 5/1495* (2013.01); *A61B 5/14532* (2013.01);
(Continued)

(58) Field of Classification Search
CPC ......... G01N 35/00693; G01N 27/3271; G01N 2035/00702; A61B 5/1495;
(Continued)

(56) References Cited

U.S. PATENT DOCUMENTS 6,233,471 B1    5/2001   Berner et al.
6,326,160 B1   12/2001   Dunn et al.
(Continued)

FOREIGN PATENT DOCUMENTS

EP    1 154 718      11/2001
WO    WO 2000/049941   8/2000

OTHER PUBLICATIONS

Passing et al., A New Biometrical Procedure for Testing the Equality of Measurements from Two Different Analytical Procedures for Method Comparison Studies in Clinical Chemistry, Part I, Journalism of Clinical Chemistry & Clinical Biochemistry, Berlin, DE, Bd. 21, Nr. 11, Jan. 1, 1983, pp. 709-720.
(Continued)

*Primary Examiner* — Tiffany Weston
(74) *Attorney, Agent, or Firm* — Bose McKinney & Evans LLP

(57) ABSTRACT

A method for operating measuring equipment for detecting at least one analyte in a bodily fluid by means of at least one continuously measuring blood glucose sensor. At least one calibration method is carried out for the prospective calibration of the measuring equipment. At least three calibration points are detected in the calibration method, wherein each calibration point comprises at least one measurement signal from the measuring equipment and at least one reference value of an associated reference measurement. A plurality of possible slopes are established between the calibration points. At least one robust estimation method, more particularly using a formation of at least one median, (Continued)

is used to determine at least one probable slope from the plurality of possible slopes. Furthermore, at least one measurement is carried out. During the measurement and using the probable slope, a concentration of the analyte in the bodily fluid is deduced from at least one measurement signal from the measuring equipment and the probable slope.

28 Claims, 4 Drawing Sheets

Related U.S. Application Data continuation of application No. PCT/EP2010/062474, filed on Aug. 26, 2010.

(51) Int. Cl.
   *A61B 5/1495* (2006.01)
   *G01N 33/66* (2006.01)
   *G01N 35/00* (2006.01)
   *G06F 17/18* (2006.01)
   *G01N 27/327* (2006.01)

(52) U.S. Cl.
   CPC ....... *G01N 33/66* (2013.01); *G01N 35/00693* (2013.01); *A61B 5/7207* (2013.01); *A61B 5/7232* (2013.01); *A61B 2560/0223* (2013.01); *G01N 27/3271* (2013.01); *G01N 2035/00702* (2013.01)

(58) Field of Classification Search
   CPC . A61B 5/14532; A61B 5/7232; A61B 5/7207; A61B 2560/0223
   See application file for complete search history.

(56) References Cited

U.S. PATENT DOCUMENTS

| | | |
|---|---|---|
| 6,424,847 B1 | 7/2002 | Mastrototaro et al. |
| 7,389,133 B1 | 6/2008 | Kotulla et al. |
| 2002/0106709 A1 | 8/2002 | Potts et al. |
| 2005/0038332 A1* | 2/2005 | Saidara ............. A61B 5/14532 600/347 |
| 2005/0143635 A1* | 6/2005 | Kamath ............. A61B 5/14865 600/347 |
| 2006/0258929 A1* | 11/2006 | Goode, Jr. ........... A61B 5/0031 600/345 |
| 2006/0264719 A1 | 11/2006 | Schurman et al. |
| 2006/0281985 A1 | 12/2006 | Ward et al. |
| 2007/0016127 A1 | 1/2007 | Staib et al. |
| 2007/0016381 A1* | 1/2007 | Kamath ............. A61B 5/14532 600/345 |
| 2008/0021666 A1 | 1/2008 | Goode, Jr. et al. |
| 2008/0081977 A1 | 4/2008 | Hayter et al. |

OTHER PUBLICATIONS

Maronna et al., Robust Statistics—Theory & Methods, 2006 John Wile & Sons, Ltd., pp. xv-xvii and pp. 1-2.
International Preliminary Report on Patentability, PCT/EP2010/062474, dated Nov. 29, 2012, English Translation.
Gather et al., Online Signal Extraction by Robust Linear Regression, Computational Statistics, 2006, pp. 1-19.
Andrew F. Siegel, "Robust Regression Using Repeated Medians", Biometrika, Jan. 1, 1982, pp. 242-244, vol. 69, Issue 1.

* cited by examiner

CALIBRATION METHOD FOR THE PROSPECTIVE CALIBRATION OF MEASURING EQUIPMENT

RELATED APPLICATIONS

This application is a continuation of U.S. patent application Ser. No. 13/405,815, filed Feb. 27, 2012, which is a continuation of PCT/EP2010/062474, filed Aug. 26, 2010, which claims priority to EP09168797.0, filed Aug. 27, 2009, both of which are hereby incorporated by reference in their entireties.

BACKGROUND

The invention relates to a method for operating measuring equipment for detecting at least one analyte in a bodily fluid, a computer program with program code for carrying out the method, and to measuring equipment for detecting at least one analyte in a bodily fluid, which is designed to carry out the method according to the invention. Such methods and devices are used, in particular, in medical technology in order to monitor, either continuously or discontinuously, one or more analytes in bodily fluids such as blood, interstitial fluid or other types of bodily fluid, for example at home or in care homes or hospitals. In particular, the method can be used for operating measuring equipment with at least one continuously measuring blood glucose sensor. Such sensors, by means of which it is possible to carry out so-called continuous monitoring, are generally implanted into fatty tissue or interstitial tissue of a user for a number of days in order to then generate measurement signals, for example at regular or irregular time intervals, from which the concentration of the at least one analyte can be deduced. The at least one analyte can, in particular, be glucose, for example blood glucose. However, in general, applications other than the aforementioned applications and the applications described below are also possible.

Since these are implanted sensors, the systems must be calibrated using already established measurement methods. Treating the error of the reference system and establishing the calibration data "in the field", i.e., without a norm, are therefore a particular challenge for these systems.

Measuring equipment for detecting at least one analyte in a bodily fluid is generally based on one or more physical and/or chemical measurement principles, by means of which one or more measurement signals are generated accordingly. By way of example, these measurement principles may be electrochemical measurement principles, by means of which one or more analyte concentrations can be detected. Such electrochemical measurement principles are known from the prior art.

However, a problem with such devices lies in the fact that, at first, the measurement signals generally are without physiological meaning. By way of example, the measurement signals may be simple currents, measured in, e.g., milliampere or nanoampere. In order to obtain information that can be used physiologically from these measurement signals, these measurement signals need to be converted into a corresponding analyte concentration by means of a suitable conversion prescription. This conversion prescription, which may for example be stored in a data processing device, is generally also referred to as calibration.

In order to apply the conversion prescription, characteristic variables (parameters) are generally required. Not all of these can be defined in advance since the sensor is implanted by the patient and hence the measurement surroundings are not precisely defined. Therefore it is necessary to carry out comparison measurements during the measurement so that the measurement signals can be very accurately converted into the analyte concentration, with no absolute norm or reference being available.

The concentration of the at least one analyte is determined in advance during a comparison measurement by means of one or more reference methods. In the following text, the disclosure will be made with reference to blood glucose as the analyte. However, alternatively or in addition thereto, it is possible to determine other types of analytes. By way of example, when determining blood glucose, the blood glucose can be determined directly by means of a chemical detection method and/or by means of another type of reference measurement, the calibration of which is already known. The measurement signals from the measuring equipment are then related to the reference values of the reference measurements for the calibration. By way of example, these can be measured current curves of continuously measuring glucose systems (continuous monitoring systems), which are related to blood glucose measurements that are measured in another way, for example individual measurements using test strips. This known relationship, which is included in a corresponding calibration, can then be used to deduce a concentration of the analyte in the bodily fluid during future measurements from measurement signals from the measuring equipment. It should be noted here that the reference measurements also have a non-negligible measurement error.

H. Passing and W. Bablok: A New Biometrical Procedure for Testing the Equality of Measurements from Two Different Analytical Methods: Application of linear regression procedures for method comparison studies in Clinical Chemistry, part I, Journal of Clinical Chemistry Clinical Biochemistry, Vol. 21, 1983, pages 709-720, have, in general, disclosed a biometric method for checking the equality of measurement values from two analytical methods. Here the use of linear regression methods in method comparison studies in clinical chemistry is described retrospectively.

The prior art has disclosed a multiplicity of calibration methods for measuring equipment, in particular for glucose measuring equipment. Here, the following text refers in particular to measuring equipment comprising at least one continuously measuring sensor, more particularly at least one continuously measuring blood glucose sensor, without this restricting possible further applications.

Many of the known methods for calibration create a correlation between the measurement signal and the glucose profile in the blood using various standard regression methods. By way of example, this can be a linear regression, a fit according to the method of least squares or the like. An example for such linear regression methods is presented in EP 1 154 718 B1. There sampled data from a glucose monitoring device are calibrated using at least one blood glucose reference read out. More particularly, it proposes calculating calibration factors using a linear regression.

A further method for calculating a relationship between the measurement signals and the reference values lies in the use of expert systems. By way of example, these are mentioned in U.S. Pat. No. 6,326,160 B1 or in U.S. Pat. No. 6,233,471. These methods use weighted sums to create a correlation between a continuously measured current profile and a blood glucose profile.

US Publication No. 2008/0081977A1 has likewise disclosed a calibration model, which in particular also takes offset times between detecting the reference values and the measurement signals into account.

US Publication No. 2008/0021666 A1 likewise undertakes the plotting of calibration data over measured data. A regression method (in this case a least squares regression) is also undertaken in this document, and this is used to calculate a slope of a fitted straight line through the calibration points.

US Publication No. 2006/0281985A1 has disclosed a method for calibrating a biosensor for detecting an analyte. Here, a multiplicity of measurement signals from the biosensor are detected over a period of time. A median filter is applied to this multiplicity of measurement signals, and the median value obtained thus is used to establish sensor sensitivity from a comparison with a measured blood analyte concentration. Here different weightings of the sensitivities can be undertaken for the different phases.

Furthermore, there often is the problem of handling the multiplicity of data in the case of real measurements, particularly in the case of continuous measurements that are undertaken over a relatively long period of time. Data compression methods, like the ones described in, e.g., U.S. Pat. No. 7,389,133 B1 or US Publication No. 2007/0016127 A1, were developed for this purpose.

However, in terms of practical handling, the presented prior art has a multiplicity of disadvantages and technical challenges. Thus, for example, most of the described calibration methods do not, or only insufficiently, account for the occurrence of outliers. Thus, for example, the calibration may yield extraordinary calibration points, i.e., calibration points which are a long way outside of the profile or value range that is expected in accordance with the remaining calibration points, and are colloquially referred to as outliers. Although these can be discarded within the scope of plausibility analysis, this can in turn lead to a falsification of the calibration.

Methods for converting the measurement signals into interpretable analyte concentrations, for example blood glucose values, should in general reproduce the profile of the analyte concentration as precisely as possible. Moreover, these methods should be robust with respect to outliers, which are created as a result of random and systematic negative influences such as temperature, movement of the user (e.g., a patient) or similar negative influences. Nor is the influence of a measurement error in the reference measurement taken into account. The known measurements only insufficiently take account of these requirements. Here, an essential point in many cases is that the measurement signal can be strongly dependent on the location and/or positioning of the actual sensor and, e.g., in the case of implanted sensors, on insertion influences. Hence a calibration in advance, as is conventional in test-strip systems, is generally unavailable.

In order to calibrate the measurement signals from continuously measuring sensors, use is therefore often made of sporadic, e.g., spaced apart by twelve hours, spot measurements, in which the calibration is for example carried out with respect to one or more reference values measured by means of test-strip equipment. However, this procedure harbors a number of challenges for the calibration. Thus, for example, although a blood glucose level, as can be measured by spot monitoring systems, and an interstitial glucose level, as can be measured by e.g., a continuously measuring, implanted sensor, are strongly correlated, they initially are two different measurement objects. In particular, dead times, which are not necessarily constant, may occur between the blood glucose profile and the interstitial glucose profile. Moreover, the blood glucose values used for the measurement can hardly be monitored in practice. While normal calibration methods have prescriptions in respect of the covered concentration range, here there often is a dependency on processing the concentration ranges prescribed by the patient. Accordingly, it may be that the concentration range, within which a calibration can be carried out, is comparatively small. Later measurements may be correspondingly imprecise if measurement signals occur outside of the calibrated range. Furthermore, the number of available calibration points is severely restricted in practice, and these calibration points harbor great uncertainty since these are generally carried out not by means of reference measurements under laboratory conditions, but by means of reference measurements using simple, everyday blood glucose equipment and under undefined measurement conditions. Likewise, the complete number of calibration points is generally only available at the end of the measurement time. However, the user generally wishes to be informed at the earliest opportunity in respect of the profile of his glucose level.

SUMMARY

The present invention provides a method for operating measuring equipment and corresponding measuring equipment that addresses the disadvantages of known methods and measuring equipment. In particular, a calibration method that is robust against outliers and reference measurement errors is taught, which calibration method allows a reliable evaluation of measurement values even under conditions that are prevalent in practice.

This advantage is achieved by a method, measuring equipment and a computer program having the features of the independent claims. Advantageous developments of the invention, which can be implemented individually or in combination, are presented in the dependent patent claims.

A method for operating measuring equipment for detecting at least one analyte in a bodily fluid is proposed in a first aspect of this disclosure. As illustrated above, this measuring equipment can more particularly detect the analyte by means of at least one continuously measuring blood glucose sensor. However, in principle, use can also be made of other types of sensors, for example sensors that, alternatively or in addition thereto, detect other types of analytes, and/or non-continuously measuring sensors.

In the method, at least one calibration method is carried out for the prospective calibration of the measuring equipment. Here, a prospective calibration should be understood to mean the establishment of a conversion prescription, which, in future measurements, allows the conversion of measurement signals from the measuring equipment, for example from at least one sensor of the measuring equipment, into a concentration of the analyte in the bodily fluid. However, in addition to at least one prospective calibration, there also is the option of carrying out at least one retrospective calibration, in which measurement signals are subsequently reevaluated and reconverted into analyte concentrations on the basis of subsequently obtained information; this is explained in more detail below.

At least three calibration points are detected in the calibration method. More than three calibration points can preferably be detected in this case. By way of example, as will be explained in more detail below, new calibration points can be added iteratively and taken into account during the calibration method. Older calibration points may optionally be discarded or given a lower weighting. Here each calibration point contains at least one measurement signal from the measuring equipment and at least one reference value from an associated reference measurement. This means that at one point at least one measurement signal from the measuring equipment is detected for establishing a calibration point. At least one reference value is detected simultaneously or with a time offset that is as small as possible (e.g., a time offset of no more than 5 minutes, preferably of no more than 1 minute) by means of a reference measurement; this reference value supplies information in respect of an actually present analyte concentration in the bodily fluid. The reference value can naturally also be afflicted by errors and should accordingly merely represent an as accurate as possible estimate or determination of the actually present analyte concentration in the bodily fluid, which is obtained by the reference measurement. The reference measurement should accordingly be carried out by means of at least one method that is known to supply measurement results that are as close as possible to the actual present analyte concentration. By way of example, this reference measurement can comprise a blood glucose measurement by means of another method, e.g., a spot measurement, in which a sample of the bodily fluid is examined once. By way of example, the reference measurement can comprise a measurement using handheld equipment. However, alternatively or in addition thereto, the reference measurement may in principle also comprise a laboratory measurement. In the following text, reference is made in particular to the reference measurement by means of one or more items of handheld equipment, more particularly by means of one or more test strips, for example using an optical and/or electrochemical detection method.

The measurement signals and the reference values are combined to form calibration points. Moreover, the calibration points may comprise further information. By way of example, the calibration points can be stored on a data medium, for example on a data medium of a computer of a control of the measuring equipment.

In principle, the measurement signals of the calibration points may be raw measurement signals, which were detected by the measuring equipment. However, these measurement signals may alternatively also already be at least partly processed measurement signals, for example measurement signals that were detected over a period of time and subsequently subjected to data processing, e.g., filtering, averaging, smoothing or a linearization transform. A linearization transform maps a nonlinear relationship between measurement signals and a concentration of the analyte onto a linear relationship. The calibration is carried out in the linearized representation, wherein, in order to represent the concentration, a transform that is complementary thereto is carried out. The linearization transform reproduces an approximate dependence between measurement signals and concentrations, which reflects properties of the measurement system. By way of example, saturation at high concentrations can reduce the sensitivity of the measuring system with increasing concentration. A logarithmic dependence between measurement signal and concentration may be assumed for this range in particular. A linearization transform transforms the measurement signals of this range in particular according to this dependence in order (approximately) to obtain a linear relationship between measurement signal and concentration. The calibration is undertaken using the linearized values of the measurement signal in order to be able to carry out the underlying observation of the possible slopes between measurement points without an error based on a nonlinear relationship. The linearization transform corresponds to the inverse function of the relationship between measurement signal and concentration. A complementary transform for converting the measurement signal into concentration values in turn corresponds to the inverse function of the linearization transform and hence to the relationship between measurement signal and concentration values that emerge from the properties of the system. The linearization transform may relate to only one interval of the measurement signal (for example, an upwardly unbounded interval, which corresponds to a saturation range of the measurement system) or it may relate to the entire range of the measurement signal. Furthermore, the linearization transform may be a function that was obtained empirically and empirically reproduces the properties of the measurement system or a function that maps at least one physical process, e.g., sensor saturation. Furthermore, the linearization transform can be represented by a polynomial or a spline, or by a series expansion, with the associated coefficients determining the transform.

Such a transform may also be used to compensate for a temporal change (degeneration) of the sensor. Here, this transform may be carried out independently of the above-described linearization step. Alternatively, the transforms presented in this section and in the preceding section can be carried out in combination, i.e., a temporal drift and non-linearity can be carried out in a (common) step using a two-dimensional transform.

It is also possible to form a median within the scope of data processing. The same also holds true for the reference values. If a plurality of reference values are available, these can also be subjected to data processing. In general, if such data processing is provided, the processed measurement signals and the processed reference values are combined to form the respective calibration points. Thus, each calibration point comprises at least one measurement signal, optionally a processed measurement signal, and at least one reference value, optionally a processed reference value.

Once the at least three calibration points have been detected, a plurality of possible slopes are established between the calibration points. By way of example, if there are three calibration points present, these are 2*3/2=3 slopes. In the case of n calibration points, there are n*(n−1)/2 possible slopes. Here, all calibration points may be taken into account such that all possible slopes are established between the calibration points. However, alternatively it is also possible to ignore one or more of the possible slopes in the calibration method such that fewer slopes are established than the aforementioned maximum number of possible slopes. However, in each case at least two slopes should be established between calibration points, preferably at least three slopes and particularly preferably more than three slopes. However, reference is made to the fact that the calibration method may optionally also be started at first with only a single calibration point being present. By way of example, the origin can initially be assumed as a further calibration point and it can optionally be discarded at a later time. These two points, i.e., a measured calibration point and an assumed calibration point, which may, for example, be the origin, can then be used to define a straight line, whose slope and axis intercept (this naturally equals 0 if the origin is selected as selected calibration point) can be determined. Alternatively, or in addition thereto, it is also optionally possible for the calibration to be started at first with two calibration points, which define a straight line. The slope a and the axis intercept b of this straight line can likewise be determined.

At least one robust estimation method is then used to determine at least one estimator for the slope of the calibration straight line, which is referred to as a probable slope in the following text, from the possible slopes between the calibration points established in this way. Here, a robust estimation method is understood to mean a statistical estimation method that still supplies stable statistical estimators even if outliers occur or even if distribution assumptions are only approximately valid.

In principle, a person skilled in the art is aware of such robust estimation methods, for example from the publication by H. Passing and W. Bablok, mentioned at the outset; however, there they are discussed within the scope of a retrospective method comparison. However, the robust estimation methods described therein may, in principle, also be applied within the scope of these teachings. In the process, it is also possible to combine different robust estimation methods. In particular, it is possible to use robust estimation methods that are based on one or more permutation algorithms and/or one or more sorting algorithms, i.e., algorithms in which values are ordered according to magnitude. A particularly preferred exemplary embodiment of a robust estimation method and more particularly of a sorting algorithm is an estimation method that uses a formation of at least one median. Accordingly, it is particularly preferred if the at least one probable slope is determined from the plurality of possible slopes by forming a median. By way of example, if n calibration points were determined, and accordingly n*(n−1)/2 slopes or fewer, however, at least two, preferably three, four or more slopes, the probable slope can be determined from these possible slopes as the median of the established slopes.

Here, the median of a series of measurements is a numerical value, for which at least half of all observations in the series of measurements are less than or equal to the median and at least half of all observations in the series of measurements are greater than or equal to the median. It follows from this definition that individual outliers do not influence the median. The median is therefore a robust estimator for the expected value of a random variable. In the case of a number of possible slopes $\{a_1, a_2, \ldots a_n\}$, which are sorted according to magnitude, the value $a_{(n+1)/2}$ is typically used as median if n is odd, and the arithmetic mean $\frac{1}{2}(a_{(n/2)}+a_{(n/2)+1})$ is used if n is even. In principle, as an alternative to using the formation of the median or in addition thereto, it is also possible to use other robust estimation methods, in particular other robust estimation methods that are based on one or more permutation algorithms and/or one or more sorting algorithms and/or on other types of robust estimation methods. It is also possible to use a combination of a plurality of different robust estimation methods.

Furthermore, at least one measurement is carried out in the proposed method. During this measurement and using the probable slope, a concentration of the analyte in the bodily fluid is deduced from at least one measurement signal from the measuring equipment and the probable slope. By way of example, it is possible to assume an offset or an axis intercept for this purpose, which offset or axis intercept can for example be obtained from an empirical value or which can be arbitrarily assumed, for example to be zero. Alternatively, or in addition thereto, it is also possible to use a probable axis intercept, which is determined according to the optional method described below. This at least one measurement signal from the measuring equipment used for the measurement may have already been used for the calibration method. However, alternatively or additionally, separate measurement signals may have been recorded during the measurement and these are then used to deduce the concentration of the analyte in the bodily fluid. As explained above, these measurement signals may for example be one or more currents, which were for example obtained by means of at least one amperometric sensor of the measuring equipment, for example when using one or more electrochemical detection methods for detecting glucose in blood, interstitial fluid or similar bodily fluids.

The inference of a concentration of the analyte in the bodily fluid from the measurement signal from the measuring equipment can for example be brought about by inverting the relationship, determined in the calibration method, between the reference values and the measurement signals. By way of example, such an inversion is generally possible in a simple fashion by forming an inverse function, at least in the case of one-to-one functions. Here, the probable slope can for example be used as so-called sensitivity and can be inverted to form the inverse function, in order to deduce the concentration of the analyte in the bodily fluid from the at least one measurement signal from the at least one measurement.

Here, the method can be carried out repeatedly and/or such that the two aforementioned method steps of the calibration method and the reference method are carried out parallel in time, overlapping in time or distributed in time.

In a particularly advantageous embodiment, furthermore, a plurality of straight lines are determined during the calibration method, the slopes of which straight lines correspond to the probable slope and respectively contain a calibration point. This plurality of straight lines is preferably determined through all calibration points, wherein, however, a smaller number than the maximum available number of calibration points can also be used. Overall, this forms a plurality of parallel lines, which each have the probable slope and run through the plurality of the calibration points. In general, these straight lines intersect the axes, e.g., the y-axis, at different points. The axis intercepts of the straight lines are determined in each case. Here, an axis intercept should be understood to mean the intersection of the straight line with the y-axis. However, another variable can also be subsumed by this term, from which variable, if need be with the aid of the probable slope, it is also possible to deduce the axis intercept, e.g., the point of intersection with the x-axis. Which axis is the x-axis and which axis is the y-axis in this representation depends on the type of plot and, in principle, can vary. Thus, by way of example, the blood glucose value or the value of the concentration of the analyte in the bodily fluid can be used as x-axis and the value of the measurement signal from the measuring equipment can be used as y-axis, or vice versa.

Thus the proposed method is preferably used to determine a plurality of axis intercepts of the straight lines. At least one robust estimation method can subsequently be used to determine at least one probable axis intercept from these axis intercepts. In principle, this may be the same robust estimation method used in determining the probable slope or in principle this may also be another type of robust estimation method. However, the use of a formation of at least one median of the axis intercepts for determining a statistical estimator of the axis intercept, which is referred to as probable axis intercept below, is once again particularly preferred. However, alternatively or in addition thereto, use can for example in general also be made of other algorithms, which are based on one or more permutation algorithms and/or one or more sorting algorithms, from which the formation of a median merely constitutes a preferred example.

If the probable axis intercept is determined in this fashion, the probable axis intercept is used during the measurement in addition to the probable slope in order to deduce the concentration of the analyte in the bodily fluid from the measurement signal from the measuring equipment. The probable axis intercept and the probable slope prescribe a uniquely prescribed linear relationship between the analyte concentrations in the bodily fluid and the measurement signals from the measuring equipment, which can also be easily inverted. However, reference is made to the fact that the probable axis intercept can also be established using a different method than using a robust estimation method, for example by a non-robust estimation method, for example by a parametric estimation method. By way of example, there may be simple averaging, for example by forming an arithmetic mean, of the axis intercepts and/or another type of straight line, which has the probable slope, through the calibration points may be used.

As illustrated above, the calibration method can more particularly be carried out repeatedly, in particular at different times. In the process, after repeating the calibration method, it is, in particular, possible to determine a new probable slope and preferably a new probable axis intercept. This new probable slope and, preferably, the new probable axis intercept can then be used in place of the previously used probable slope and the previously used probable axis intercept in at least one subsequent measurement in order once again to deduce the concentration of the analyte in the bodily fluid from at least one measurement signal.

The proposed method can furthermore be combined with known methods. Thus, for example, plausibility analysis can be carried out during the calibration method. Here, the plausibility analysis is an inspection in which values that lie outside a prescribed range are not taken into account. By way of example, the prescribed range may contain empirical values. Thus, unrealistic calibration points and/or unrealistic slopes and/or unrealistic axis intercepts may be discarded in the plausibility analysis. The calculation may also be carried out iteratively with a number of subsets of the calibration points, for example using a "leaving-one-out" method in order to examine the dependence of the probable slope or of the probable offset on a calibration point.

Furthermore, at least one current calibration quality may be determined in the proposed method. In principle, a calibration quality should be understood to mean at least one indicator that specifies the uncertainty inflicted on the current calibration, i.e., the uncertainty in the deduction of the concentration of the analyte in the bodily fluid from a measurement signal when using the current calibration. In particular, the calibration quality may comprise at least one confidence interval, i.e., a standard deviation, for example, or a multiple of the standard deviation.

The change of the determined slope and of the axis intercept compared to the preceding calibration can also be used as a test statistic in this case as to whether the sensor still has the required sensor properties. By way of example, this is how outliers are identified, with these then being discarded as a calibration result in order to carry out a new calibration. If the slope of a current calibration differs from the slope of the preceding calibration or from the slopes of the preceding calibrations by more than a predetermined measure (corresponding to the confidence interval), the current calibration is discarded and a new calibration is carried out (i.e., the calibration is repeated).

The method can furthermore be carried out such that a user is, preferably automatically, invited to carry out the calibration method. Here, a distinction can optionally be made between different states, e.g., a recommendation of a further recording of a reference value with the aid of a conventional blood glucose measurement for improving the calibration or the mandatory recording of a reference measurement, with the system being shut down if this calibration is not carried out within a defined period of time. By way of example, this invitation can be brought about by means of at least one optical and/or acoustic and/or haptic indication, which invites the user to carry out the calibration method. In particular, this invitation may be brought about automatically, for example by means of a control of the measuring equipment.

In particular, the user can be invited to carry out the calibration method if at least one calibration condition is present, i.e., a condition that makes carrying out the calibration method appear to be expedient. In particular, this condition may consist of the fact that at least one current measurement signal lies in a range in which a calibration quality lies below a predetermined quality threshold. By way of example, this may be as a result of the fact that there are yet to be a sufficient number of calibration points in this region, for example because no measurement signals occurred in this region until now. This method variant takes into account the fact that, contrary to laboratory trials, analyte concentrations for the calibration cannot be prescribed arbitrarily in practical use in a user, but rather that the calibration needs to be carried out using the analyte concentrations actually occurring in the user. By way of example, if the case then occurs that a value for an analyte concentration is present that has not been present previously, the user can be automatically informed that now is an expedient time to carry out a calibration method. If a current calibration quality is determined, a user can more particularly also be informed if a current measurement signal is in a region of insufficient calibration quality. In this case there can, for example, once again be an optical, an acoustic or a haptic indication or signal to the user. This user can also be informed that a measurement of the analyte concentration is terminated or interrupted automatically, optionally together with a note that there is insufficient calibration quality, which may also include an upward or downward deviation from a valid region.

As set forth above, the calibration method can in particular be carried out repeatedly, for example at regular or irregular intervals, for example as a result of an invitation by the measuring equipment. The calibration information newly obtained in this case, for example a new probable slope, can then be used for the prospective evaluation of future measurements. However, alternatively or additionally, there can also be a retrospective evaluation of measurements already carried out, and so these measurements can be newly evaluated. If the calibration method and/or parts of the aforementioned calibration method are carried out repeatedly, for example by only newly determining individual new calibration points, older calibration points can then also be discarded. As explained above, this discarding may either involve completely ignoring these older calibration points or at least a lower weighting of these older calibration points. By way of example, older calibration points can be understood to mean calibration points that are older than at least one prescribed time threshold.

Specific embodiments of the method distinguish between the following states:
 (A) Mandatory reference measurement (i.e., calibration), "Must calibrate"
 (B) Recommended reference measurement, "Recommend to calibrate"
 (C) Ready for a reference measurement, "May calibrate" or "Ready to calibrate" and (D) Good conditions for a reference measurement, "Nice to calibrate".

(E) Calibration impossible due to bad signal properties, "Must not calibrate"

In state (A), a display of measurement results is blocked, for example, in order to force the user to undertake a calibration. This state is left as a result of a successful calibration or reference measurement, and a measurement, including the display of the resultant measurement results, is made possible, wherein the measurement is based on the successful calibration or reference measurement. State (A) occurs if the most recent calibration/reference measurement dates back longer than a predetermined period of time or if there has yet to be a calibration/reference measurement using the present measurement system. State (A) can furthermore occur if the measurement signal lies in a region outside of a predetermined, conventional measurement range and indicates a fault, e.g., a contact fault. State (A) does not occur if the measurement values lie below a predetermined boundary, with the boundary indicating a critical state of the measurement object, e.g., hypoglycemia. In the case of measurement values that lie below this boundary, a different state, in which measurements are carried out and displayed, is necessarily called, preferably state (B) or else states (C) and (D). In states (B), (C) and (D) (and also (E)), it is possible to carry out measurements and display the results thereof. Furthermore, state (A) can be terminated if it lasts for longer than a predetermined length; the measurement is preferably terminated in this case.

State (B) displays an invitation to calibrate or the user is informed of the necessity of a calibration/reference measurement. State (B) occurs if a measurement signal lies outside of the calibration range, i.e., outside of the reference points of the reference measurement. State (B) preferably occurs if the measurement signal lies outside of a range emerging from the calibration range, an adjoining lower tolerance range and an adjoining upper tolerance range. The upper tolerance range, which adjoins the calibration range in the direction of the higher values (i.e., it adjoins the largest value of the reference measurements), has a width corresponding to a prescribed proportional factor multiplied by the upper boundary of the calibration range or multiplied by the measurement signal. The width of the lower tolerance range is preferably prescribed by an absolute value. Finally, state (B) may be entered if a prescribed period of time has elapsed since the last calibration. This period of time is shorter than the period of time used in the context of state (A). State (B) corresponds to a calibration that still is valid, but the accuracy of which is low, which is why a calibration with a higher precision should be carried out.

State (C) corresponds to a standard state, which represents the general readiness of the device for calibration, for example if a calibration has already been carried out. State (C) corresponds to a state in which a calibration does not necessarily lead to an improvement in the measurement accuracy, contrary to states (A) and (B).

State (D) is entered if the conditions are particularly favorable for a precise calibration/reference measurement. This is satisfied if the measurement results (over a predetermined period of time) fluctuate by less than a predetermined range of fluctuation. In other words, this is satisfied if the dynamics of the measurement results lie below a specific threshold. The low dynamics or variations indicate a stable state or a high significance of the reference measurement, wherein this in turn is linked to high accuracy. In state (D), information is displayed that there are good calibration conditions or there is the possibility of improving the measurement precision.

State (E) is entered if the signal properties make it possible to deduce high variation or a significant current change in the signal (i.e., the measurement values), which lies above a predetermined maximum variance or maximum change. In state (E), the currently valid calibration/reference measurement would be replaced by a less precise value as a result of the variation or as a result of the significant trend (large increase or decrease in the measurement signal over the relevant period of time) because the significant variation/the large increase is linked to a large error. It is indicated in state (E) that a calibration should not be carried out. Furthermore, commands to undertake a calibration, to the extent that they nevertheless are entered, are ignored in state (E) and the previous reference measurement/calibration is kept. Measurements can be carried out in state (E) and the measurement result is displayed. It is optionally possible to indicate that the measurement should be repeated (particularly after a calibration outside of the state (E)) and/or that the measurement result is not very precise. The current calibration is used in the measurement, with a calibration command entered in state (E) leaving the current calibration unchanged. In state (E), use is made of a calibration that was carried out prior to the entry into state (E) (i.e., the reference measurement of which calibration was carried out before entering state (E)).

States that indicate particularly high dynamics or variation (e.g., state (E)) and states that indicate particularly low dynamics or variation (e.g., state (D)) are preferably identified by observing the temporal or stochastic property of the measurement signal itself. In this case, a calculation is made either of a value corresponding to a variance or variation or a calculation is made of a value that reproduces the first time derivative, or both. Compared to the corresponding boundary values, this value (these values) serve(s) as a basis for the decision as to whether particularly high/low dynamics or variation is present. In particular, these values can reproduce the maximum of the dynamics (i.e., the first derivative) or of the variation in the measurement signal. The observation of the measurement signal preferably relates to a time window of the measurement signal or to the last N values of the measurement signal, wherein N is a natural number>0 (preferably >10, >100 or >1000).

In addition to a start or end state, the method preferably provides for substantially only switching between states (A)-(E).

Furthermore, the method can also be modified such that the calibration points and/or components of the calibration points, for example the measurement signals and/or the reference values, are, either individually or together, subjected to a smoothing method. As an alternative to applying a smoothing method during the calibration method, or in addition thereto, the at least one measurement can also take place with one or more smoothing methods being carried out. By way of example, the calibration points and/or the measurement signals can be subjected to at least one smoothing method, more particularly a smoothing method by means of at least one exponential filter. Exemplary embodiments of such smoothing methods will be explained in more detail below.

Furthermore, the method can be developed such that the calibration points and/or components of these calibration points and/or the measurement signals are subjected to at least one linearization step. An at least approximately linear relationship between the measurement values and the reference values can be produced in this linearization step. This method is particularly expedient if a nonlinear relationship is determined or known to exist between the analyte concentration and the measurement signals. By way of example, the signal profile of the measurement signals can exhibit saturation behavior, i.e., have a downward deviation from a linear profile in the case of relatively high values of the measurement signals in particular. In this case, the aforementioned linearization step can be undertaken before evaluating the calibration points and/or before evaluating the measurement signals. Here, the calibration points and/or the measurement signals can for example be subjected to a transform, which, as is well known, in turn produces a linear profile. In the case of saturation behavior, this can for example be brought about using at least one logarithm, particularly in the case of measurement values within a prescribed saturation range, in which a partial saturation of the measurement system may be assumed. Examples of linearization steps are illustrated above and will be explained in more detail below.

Furthermore, a method for operating measuring equipment for detecting at least one analyte in a bodily fluid is proposed, which method comprises a data reduction. In principle, this method can be embodied as a development of the above-described method in one or more of the illustrated method variants, and so the features described below may be considered to be additional features. However, alternatively the method described below can also be realized independently, without the above-described method features of the first aspect of this disclosure.

In this second aspect of a method for operating measuring equipment for detecting at least one analyte in a bodily fluid, a plurality of measurement signals of the measuring equipment are, in a measurement, detected over a measurement period. By way of example, this measurement period may comprise a typical measurement period of a continuously measuring blood glucose sensor, for example of the order of minutes, in which, for example, measurement signals are in each case detected in sub-minute intervals.

Furthermore, at least one data reduction is carried out. During this data reduction, the plurality of measurement value pairs, consisting of measurement signal and measurement time, are reduced to one or a few measurement value pairs. In the process, one or more of the following data reduction methods may be applied.

In a first possible data reduction method, at least one robust estimation method is used to determine at least one probable measurement signal for the measurement time period from the plurality of measurement signals. The plurality of measurement signals are then replaced by the probable measurement signal. In respect of the robust estimation method, reference can be made to the above description of robust estimation methods. Once again, use can also be made of a combination of robust estimation methods. The use of a median is particularly preferred. However, alternatively or additionally, use could in general for example be made of other algorithms as well, which are based on one or more permutation algorithms and/or one or more sorting algorithms, from which the formation of a median merely constitutes a preferred example.

Alternatively, or in addition thereto, the data reduction method can also be carried out in such a way that the measurement signals with the associated measurement times are combined to form measurement value pairs. The measurement value pairs can moreover comprise additional information. Furthermore, a plurality of possible slopes between the measurement value pairs are established, with a probable slope being established from the plurality of possible slopes by means of at least one robust estimation method. Once again, the statements made above in respect of the robust estimation method analogously hold true. In particular, this robust estimation method can once again be carried out using at least one median. However, alternatively or additionally, use could in general for example be made of other algorithms as well, which are based on one or more permutation algorithms and/or one or more sorting algorithms, from which the formation of a median merely constitutes a preferred example.

A plurality of straight lines through the measurement value pairs are then formed from the plurality of possible slopes. By way of example, this can be brought about by virtue of the fact that straight lines are formed through each point corresponding to a measurement value pair, or at least through a plurality of these points, which straight lines have the probable slope such that a host of parallel straight lines through the points is created. Furthermore, at least one representative time is selected for the measurement time period, for example the middle of the time interval of the measurement time period. However, in principle, the representative time can be selected at any point within the measurement time period, for example the start point or the end point of the measurement time period, or any intermediate point. Subsequently, the functional values of the aforementioned straight lines, i.e., of all or a plurality of the straight lines, are determined for the representative time, with at least one probable functional value being established from the functional values by means of at least one robust estimation method. Then the plurality of the measurement value pairs are replaced by at least one representative measurement value pair, which comprises the at least one probable functional value and the at least one representative time. In particular, the robust estimation method can once again be carried out using a formation of at least one median. However, alternatively or additionally, use could in general for example be made of other algorithms as well, which are based on one or more permutation algorithms and/or one or more sorting algorithms, from which the formation of a median merely constitutes a preferred example. Examples of the described data reduction method will be explained in more detail below.

At least one measure of variation can furthermore be determined during the data reduction, in one or both of the described variants, from the plurality of measurement signals, more particularly a standard deviation and/or a measure of the quantile.

Furthermore, it proves possible during the data reduction methods, in particular during the second variant of the data reduction method, to determine a trend from the plurality of measurement signals. This trend, which predicts a time profile of the measurement signal on a continuous or ordinal scale, can more particularly be established from the probable slope, which, on its own, already specifies such a trend. For example, the measurement points taken every second can be combined to form a single measurement point every minute by averaging (optionally with exclusion of outliers).

Furthermore, at least one statement in respect of a signal quality of the plurality of measurement signals can be made during the method. In particular, this statement in respect of the signal quality can be made by a comparison between robust estimators of the measurement signals, e.g., once again, of the median (and/or another permutation algorithm and/or sorting algorithm) and/or the measures of the quantile, and parametric estimators of the measurement signals, e.g., of the mean and/or the standard deviation.

In a third aspect, a method for operating measuring equipment for detecting at least one analyte in a bodily fluid is proposed in turn. The method can once again additionally have the features of the above-described method variants as per the first and/or second aspect, and so reference can be made to the description above for possible further embodiments of the third aspect described in the following text. However, the third aspect can also be carried out independently of the above-described embodiment variants.

Concerning the third aspect of these teachings, a calibration of measurement signals from the measuring equipment is carried out against reference values of associated reference measurements during at least one calibration method. This can be one or more reference measurements. Reference can be made to the description above in respect of possible embodiments of the reference measurements. Furthermore, a calibration strategy is applied in the method in the third aspect of the invention. In general, a calibration strategy should be understood to mean a strategy for optimizing the calibration, for example for continuously improving the accuracy of the calibration, for example a calibration quality.

The calibration strategy may comprise one or more of the method steps described in the following text.

Thus, depending on a current calibration quality emerging, for example, from plausibility analysis, a region of measurement signals from the measurement region can be restricted, which region can be used for the measurement. Thus, for example, a region that is covered with sufficient calibration quality by the previous calibration may be determined as a region that can be used. By way of example, this may be a region within which reference values are present, optionally with one or more additional intervals above or below this region, for example with dimensions of a prescribed percentage. In particular, a user can be informed if measurement signals are detected outside of a region that can be used, for example information can be provided that a lower boundary was undershot or that an upper boundary was overshot. By way of example, this can once again be brought about by an optical, an acoustic or a haptic indication.

Alternatively, or in addition thereto, the calibration strategy can also include an invitation to a user to carry out the calibration method again. By way of example, this invitation can once again be made via an indication element, for example if the previous calibration quality is insufficient and/or if this is an expedient time to carry out a calibration method.

In another alternative or in addition thereto, the calibration strategy can also comprise a method step in which a user is informed that this is an expedient time to carry out the calibration method. In particular, this information can once again be provided by an indication element. As already explained above, an expedient time can be present, in particular, in the case when signal dynamics of the measurement signals are currently low and/or in the case when a large deviation in the concentration of the at least one analyte in the bodily fluid is expected compared to previous analyte concentrations.

In another alternative or in addition thereto, the calibration strategy can also comprise a method step in which a user is invited to carry out the calibration method or to carry it out again at regular or irregular intervals, e.g., at prescribed intervals. By way of example, such an invitation may occur after a prescribed number of hours have elapsed since the last time the calibration method was carried out.

In addition to the method according to one or more of the above-proposed embodiments, a computer program with program code for carrying out the method according to one or more of the proposed variants when the program is executed on a computer is furthermore proposed. In particular, the computer program can be carried out on a computer of a control of the measuring equipment for detecting at least one analyte in a bodily fluid. The computer program can more particularly be stored on a computer-readable data medium.

In addition to the method and the computer program, measuring equipment for detecting at least one analyte in a bodily fluid is furthermore proposed. The measuring equipment can in particular comprise at least one continuously measuring sensor, more particularly a continuously measuring blood glucose sensor. The measuring equipment is designed to produce at least one measurement signal corresponding to a concentration of the analyte in the bodily fluid. The measuring equipment is furthermore designed to receive reference values detected by means of an independent reference measurement. The measuring equipment has at least one control, more particularly a control with at least one computer, wherein the control is designed to carry out a method according to one or more of the above-described method variants. Here, the measuring equipment may comprise one or more components, which may be embodied in a connected or non-connected fashion. Thus, for example, the measuring equipment can comprise a plurality of individual items of measuring equipment, i.e., have a decentralized design, wherein the individual items of measuring equipment interact within the meaning of the measuring equipment according to the invention. By way of example, these could be the continuously measuring sensor and control equipment and/or further measuring equipment, which may be in communication with one another in a wired or wireless fashion. Accordingly, measuring equipment can also be understood to mean a measuring system with a plurality of individual components, preferably with a plurality of components that are connected to one another via a communication link. However, alternatively, integration in a single item of measuring equipment is also possible.

The proposed method, the computer program and the measuring equipment in one or more of the above-described embodiment variants have a number of advantages over known methods and devices of this type. Thus, in particular, it is possible to achieve a stable calibration, which is also comparatively insensitive in respect of outliers. In contrast to the method described in US Publication No. 2006/0281985, for example, in which median calculations are only used for the measurement values, according to this disclosure, a regression is used directly for the calibration method as per a first aspect of this disclosure. The probable slope established in the process reflects the sensitivity of the measuring equipment, e.g., of the measuring system. The method can be implemented in a simple and quick fashion and is particularly suitable for continuously measuring blood glucose measuring equipment, in which the above-described difficulties may occur during the calibration.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

Figure 1:
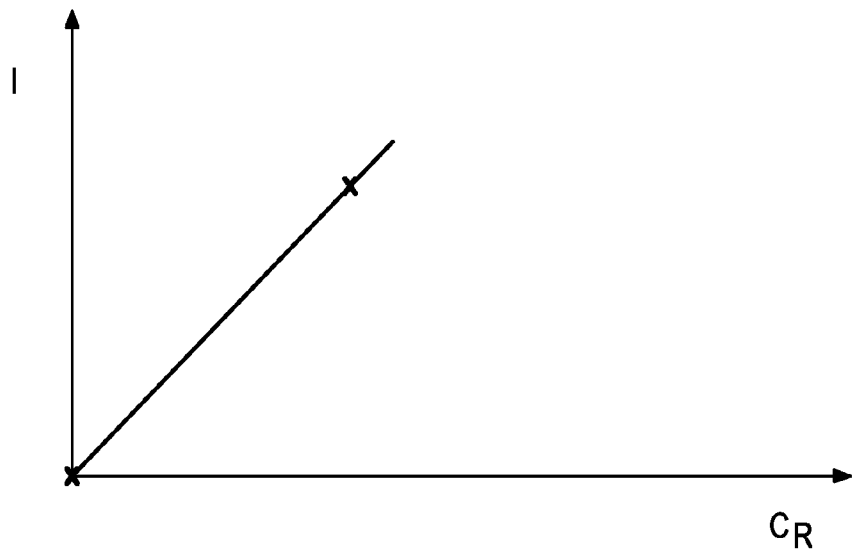
FIGS. 1A-1D show method steps of a first exemplary embodiment of a method with a calibration method for determining a probable slope and, optionally, a probable axis intercept.
Figure 1:
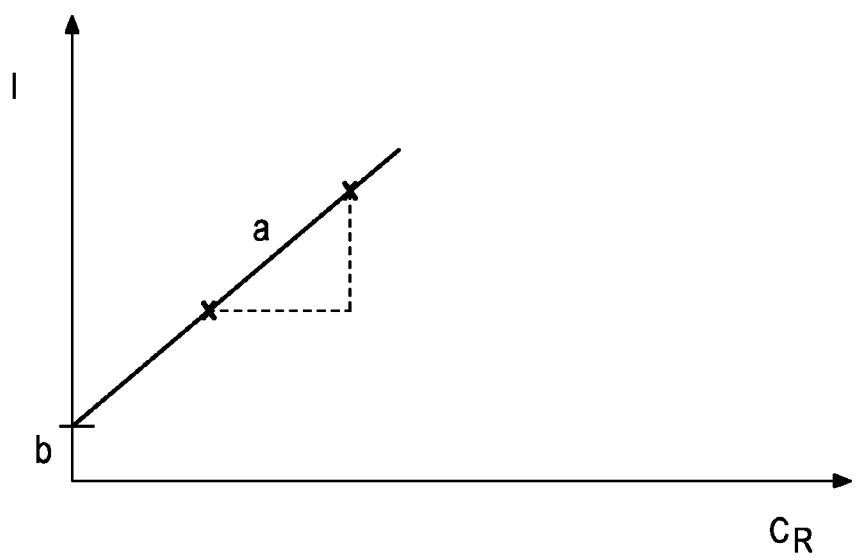
Figure 1:
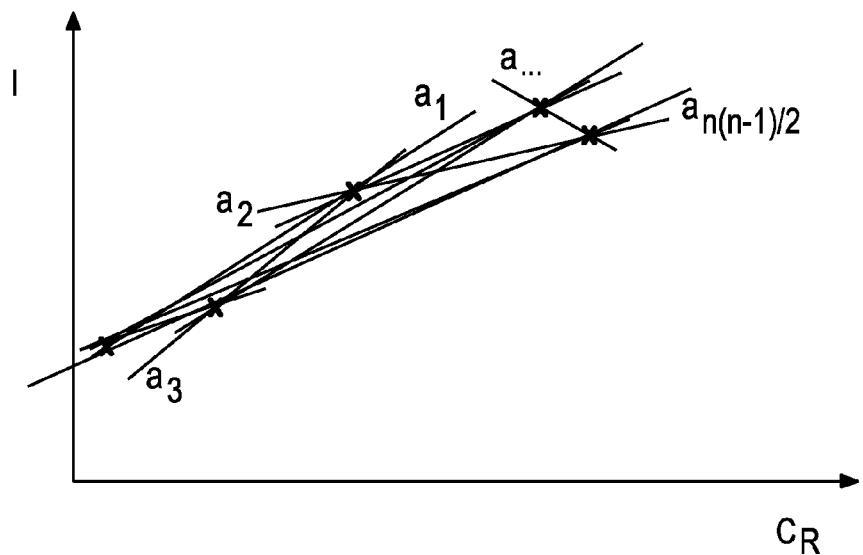
Figure 1:
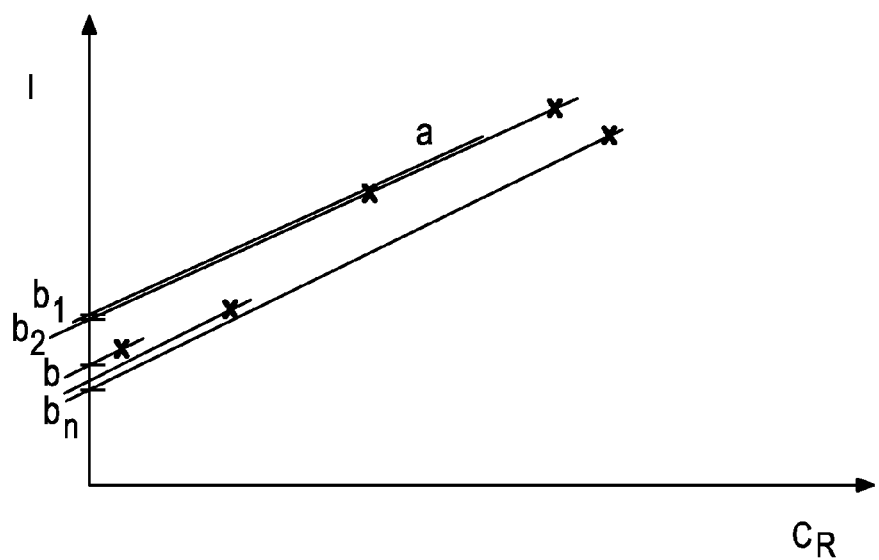

The embodiments described below are not intended to be exhaustive or to limit the invention to the precise forms disclosed in the following detailed description. Rather, the embodiments are chosen and described so that others skilled in the art may appreciate and understand the principles and practices of the present invention.

In the following text, FIGS. 1A to 5 should be used to illustrate exemplary embodiments of a method and of measuring equipment 110, for detecting at least one analyte in a bodily fluid. FIG. 5 schematically illustrates an exemplary embodiment of such measuring equipment 110. In this case, the measuring equipment is measuring equipment for continuous blood glucose monitoring by means of a continuously measuring blood glucose sensor 112. By way of example, this continuously measuring sensor can be implanted into interstitial tissue of a user and remain there over a period of time of, e.g., a number of days. The measuring equipment 110 furthermore comprises a control 114 with at least one computer 116. Furthermore, the measuring equipment 110 can comprise one or more indication elements and/or one or more operating elements, and, optionally, one or more interfaces for allowing interaction between the measuring equipment 110 and a user and/or other equipment, e.g., a computer or a computer network. As indicated by the reference sign 118 in FIG. 5, the control 114 is connected to the continuously measuring blood glucose sensor 112 in a wireless or wired fashion.

Furthermore, the measuring equipment 110 is designed to receive one or more independently detected reference values. This reception of reference values is characterized by reference sign 120. In order to produce the reference values, provision can be made for separate reference measuring equipment 122, for example test-strip measuring equipment for the spot measurement of blood glucose values in drops of blood. Alternatively, or in addition thereto, the reference measuring equipment 122 can also be wholly or partly integrated into the measuring equipment 110 itself. This should also be encompassed by the phrase receiving reference values.

FIGS. 1A to 1D illustrate an exemplary embodiment of a calibration method for prospective calibration of the measuring equipment 110. An at least approximately linear relationship between the measurement signals from the measuring equipment and the reference values from reference measurements is assumed for the calibration method. Alternatively, in the case of a nonlinear relationship, a linear relationship (i.e., a linear profile of the measurement value—concentration line) can be produced by a fixedly prescribed, nonlinear transform, more particularly as a preceding linearization step or linearization transform of the measurement values or of the measurement signal, before these are or it is considered on the basis of the slopes. In particular, use can be made of the above-described linearization transforms. The measurement signals from the measuring equipment are denoted by I in FIGS. 1A-1D and are, in an exemplary fashion, specified in ampere. However, in principle, any units and/or variables may be used as measurement signals. Here, the measurement signals I are plotted on the y-axis in FIGS. 1A-1D. By contrast, the reference values are denoted by $c_R$ in FIGS. 1A-1D and are specified in arbitrary concentration units. By way of example, these can be reference values that were established by means of reference measuring equipment 122 in the form of handheld equipment, e.g., analogously to FIG. 5. However, alternatively or in addition thereto, these reference values can also, as illustrated above, be established by the measuring equipment 110 itself by means of a reference measuring method, for example by integrating such reference measuring equipment 122 into the measuring equipment 110. The above-described linear relationship between the measurement signals from the measuring equipment and the reference values is assumed to hold at least in a measuring range, for example within a measuring range that is usually not undershot or overshot.

A goal of the calibration method is to determine the aforementioned relationship. A linear relationship is defined by a slope a and an axis intercept b of a linear function with the functional equation $I = a*c_R + b$. In order subsequently to an analyte concentration c, e.g., a blood glucose concentration, from a measurement signal from the measuring equipment 110 during an actual measurement, the aforementioned linear equation should be inverted, and so the equation $c = (1/a)*I - b/a$ can be applied. Thus, the parameters a and b determine a calibration of the measuring equipment 110.

Thus, during prospective calibration, calibration points are determined, optionally iteratively, which calibration points respectively comprise a measurement signal from the measuring equipment 110 and at least one reference value. The slope a and the axis intercept b are calculated from these calibration points, for example according to the method described in the aforementioned publication by H. Passing and W. Bablok.

In order to ensure a quality of the parameter calculation that is as high as possible, the selection of the reference values is controlled by the reference measuring equipment in a preferred embodiment. In particular, a reference value is not used for calibration (i.e., excluded) if the associated signal from the measuring equipment has low quality (large variation of the measurement values) or high dynamics (trend). By contrast, the user is invited to perform a calibration if the signal converted using the previously established calibration parameters leaves the range covered by the already recorded calibration values. This range or tolerance range can for example be given by the interval $[c_{lb}: c_{ub}]$, with:

$$c_{lb} := \min\{bG_{min} - Cp*d; bG_{min}*(1-d)\} \text{ and } c_{ub} := \max\{bG_{max} + Cp*d; bG_{max}*(1+d)\}$$

Here, Cp is a prescribed, characteristic measurement point, d is a prescribed tolerance and $bG_{min}$ and $bG_{max}$ are the minimum and maximum recorded reference value. The tolerance d used here is relative and brings about a tolerance width determined by the respective reference value. It is alternatively possible to determine the lower boundary $c_{lb}$ by the minimum reference value minus a prescribed, absolute tolerance-width value. If a measurement value occurs below the interval, neither a measurement nor a display of the measurement result is blocked. Instead, the measurement result is indicated and there is an invitation to carry out the calibration or to repeat the measurement. In particular, this is carried out in cases in which a measurement value corresponds to a concentration that is typically considered to be hypoglycemic (provided blood glucose is detected as an analyte). This prevents a hypoglycemic measurement from not being carried out or the results thereof not being displayed because the calibration strategy in this case (outside of the tolerance range, i.e., outside of the calibrated range) necessarily requires a further calibration (cf. state (A)) before a measurement value is output.

FIG. 1A shows a first step, in which there merely is a single calibration point. By way of example, the origin can be assumed to be a further calibration point. A straight line is defined by these two points, i.e., a measured calibration point and an assumed calibration point, which may for example be the origin, wherein the slope and the axis intercept (naturally equal to 0 if the origin is the selected calibration point) of this straight line can be determined.

Two calibration points, which define a straight line, are already known in FIG. 1B. The slope a and axis intercept b of this straight line can likewise be determined.

FIG. 1C illustrates the method if a multiplicity of calibration points are known; in this case n calibration points. Straight lines can then, as illustrated in FIG. 1C, be formed between all of these calibration points or between a plurality of these calibration points, wherein the slopes $a_i$ (with i=1, ... n) of these straight lines can be determined. Thus, in the case of n calibration points, there are at most $n*(n-1)/2$ possible slopes a.

In the proposed method, the median is then formed from all or at least a plurality of possible slopes $a_1$ to at most $a_{n*(n-1)/2}$, which median is referred to as probable slope a; for example, $a=\text{median}\{a_1, a_2, \ldots, a_{n*(n-1)/2}\}$. However, alternatively or additionally, other algorithms could, for example, also be used in general, which algorithms are based on one or more permutation algorithms and/or one or more sorting algorithms, from which the formation of a median merely constitutes a preferred example; this has already been illustrated above. However, alternatively or additionally, use can in principle also be made of other robust estimation methods.

The probable slope a established thus can already be used in subsequent measurements, for example by using a straight line through the origin with the inverse of this slope for converting a measurement signal from the measuring equipment 110 into a blood glucose concentration. However, it is particularly preferred if an axis intercept b is additionally also established, the latter describing an offset. This is illustrated in FIG. 1D as an optional method step. In this method step, a straight line with the probable slope is placed through each of the calibration points or at least through a plurality of the calibration points. The axis intercept $b_i$ of this straight line is determined, in particular calculated according to the equation $b_i = y_i - a*x_i$. Here $x_i$ and $y_i$ denote the reference measurement and the measurement signal of the i-th calibration point. Using this plurality of axis intercepts $b_1, \ldots, b_n$, i.e., a plurality or all of these axis intercepts, it is once again possible to determine a probable axis intercept b, for example according to the equation $b=\text{median}\{b_1, b_2, \ldots, b_n\}$ using an estimation method, preferably a robust estimation method, more particularly a robust estimation method using a median.

The linear relationship between the reference values and the measurement signals is fully known using the probable slope a and the probable axis intercept b. In order to deduce a concentration of the analyte in the bodily fluid from a measurement signal in a following measurement, all that needs to be done is to invert this linear relationship, for example according to the above-described equation $c=(1/a)*I-(b/a)$.

The method, described using FIGS. 1A to 1D, with the calibration method can also be carried out repeatedly. In particular, the method can be carried out such that a regression as per the aforementioned publication by H. Passing and W. Bablok is carried out with every newly added calibration point with a measurement value pair. In this respect, reference can for example be made to the aforementioned publication. In conclusion, the method can thus for example be carried out as follows:

1. Start: If 2 calibration points or measurement pairs (e.g., continuous measurement current I, blood glucose reference value $c_R$) are present, a slope and the axis intercept are calculated.

2. If an additional calibration point in the form of a measurement pair is added, proceed as follows:
   a. Calculate the additional slopes between the available pairs.
   b. Form the median from a plurality of, preferably all, slopes calculated thus (in the case of 3 pairs, there are $2*3/2=3$ slopes; in the case of n points, there are $n*(n-1)/2$). This median is used as new value for the probable slope of the calibration straight line.
   c. Place a straight line with the probable slope, calculated in 2b), against each calibration point.
   d. Calculate the intersection with the y-axis (x=0) for a plurality of points, preferably for every point.
   e. Calculate the median of all axis intercepts calculated thus. This is a new estimated value for the probable axis intercept of the calibration straight line.

3. The calibration straight line calculated thus serves for converting measurement signals into blood glucose values until a further calibration pair is available. Then go to 2.

By prescribing a reference point (e.g., an expected current value in the case of a glucose concentration of 0 mg/dl), this method can in principle also implement a single-point calibration, as illustrated in FIG. 1A.

As a result of using robust median estimators, the method offers the advantage of being robust against outliers and measurement errors. In principle, an evaluation of the quality of the recorded calibration point is no longer necessary, but it may optionally be carried out additionally.

The method described above using FIGS. 1A-1D can be developed by various embodiments. One option consists of applying a data compression, although the latter can, in principle, also be utilized independently. Such data compression can be used both in the calibration method when determining the calibration points and during the actual measurement in which an analyte concentration in the bodily fluid is deduced, or during one of these method steps.

A first method for reducing the amount of data consists of forming a median from a plurality of individual measurement signals. Thus, in order to reduce the amount of data for calibration and/or for evaluation, there can be a compression of measurement signals, which were for example recorded in the sub-minute range, for example to values in the minute range. To this end, a plurality of measurement signals can be recorded for the respective measurement time period. Here n specifies the number of utilized values in the sub-minute range. Then, e.g., the median can be calculated from these values, i.e., the individual measurement signals of the measurement time period, and can be used as compressed value for the respective value in the minute range. By way of example, this compressed measurement signal can then be used in the calibration method and/or during the actual measurement. It is likewise possible to calculate measures of variation, e.g., the standard deviation and/or the measure of the quantile, in the time interval of the measurement time period. By way of example, the signal state can be derived from these measures of variation. In this respect, reference can for example also be made to U.S. Pat. No. 7,389,133 B1 and US Publication No. 2007/0016127 A1. By making a comparison between the robust estimators, e.g., the median and/or the measures of the quantile, and parametric estimators, e.g., the mean and/or the standard deviation, it is likewise possible to make statements in respect of the signal quality.

A second method for data compression, which can be used alternatively or additionally and, e.g., is once again in the minute range or based on another measurement time period, can be carried out by renewed application of a regression method using one or more robust estimation methods. By way of example, to this end, analogously to the aforementioned description of FIG. 1C, possible slopes between all or a plurality of the measurement signals of the measurement time period, for example all or a plurality of slopes between respectively two values in the sub-minute range, can be calculated from the plurality of measurement signals in the measurement time period to be compressed, and the median of all slopes can subsequently be determined. Straight lines with this median slope, which once again constitutes an example of a probable slope, can be placed through all or a plurality of current-time points in the measurement time period and in each case it is possible to calculate or determine the value of this straight line at a specific time, which is selected as representative time for the measurement time period, e.g., the middle of the period of time. The median of all current-time estimators calculated thus at the representative time, at which the evaluation is carried out, is the measurement value for this measurement time period. This principle is also referred to as repeated median principle. The calculated slope of the straight line, i.e., the probable slope, can moreover be considered as a measure of the trend for this measurement time period.

Figure 2:
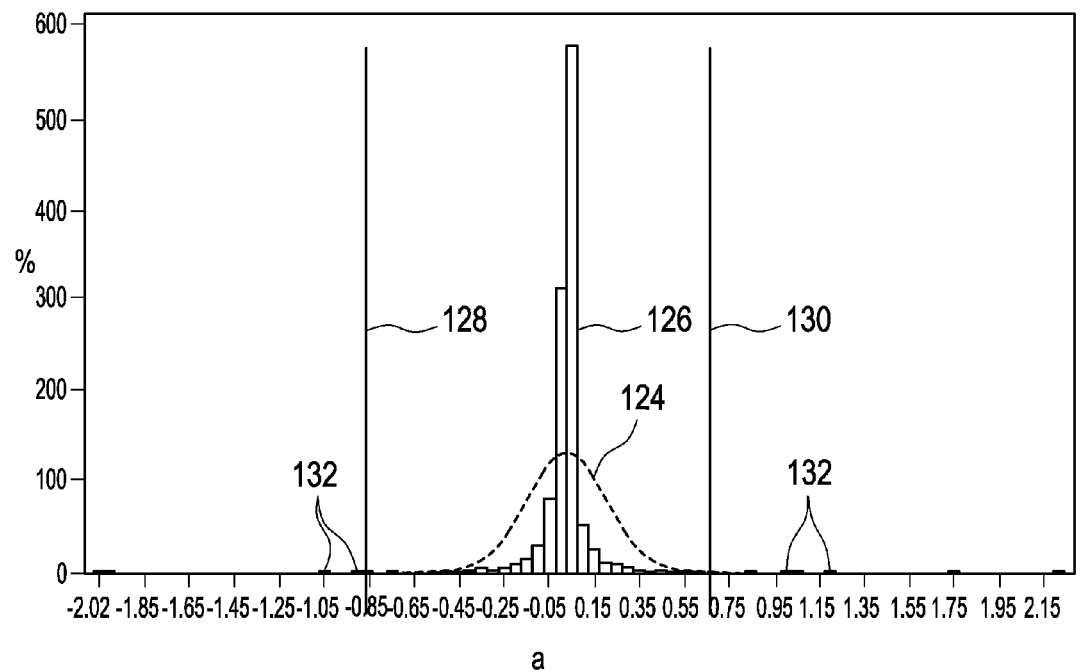
FIG. 2 shows an exemplary embodiment of carrying out plausibility analysis.

In a further possible embodiment of the method, which should be explained on the basis of FIG. 2, it is possible to assess the calibration quality. Thus, for example, confidence intervals can be calculated to assess the current quality of the calibration. This makes it possible to estimate if and when a further calibration must be carried out, i.e., if and when the above-described calibration method needs to be carried out again. Furthermore, an estimation is made possible as to whether the range (i.e., range or tolerance range), i.e., the difference between the maximum value of the analyte concentration and the minimum value of the analyte concentration, which is used to carry out the calibration method, is sufficient for a reliable calibration. It is also possible to restrict in advance the range of the slopes allowed for the calculation.

It is likewise possible to exclude old calibration points, the recording time of which lies further back than a fixedly prescribed time interval, from the calibration and thus compensate for a temporal change in the system because in this case a new calibration is invited or forced.

Thus, FIG. 2 plots a possible statistical distribution of the established slopes in a histogram 126. Here, the y-axis denotes the number N of counts of a specific slope, whereas the slope is plotted on the x-axis. It is likewise possible to identify from FIG. 2 that a lower threshold 128 and/or an upper threshold 130 can be prescribed, with outliers (denoted by reference sign 132 in FIG. 2, i.e., slopes outside of the region prescribed by the thresholds 128, 130) being discarded, which can consist of these values being completely ignored or only being provided with a very low weighting. This makes it possible to avoid an erroneous calibration by restricting the range of admissible slopes for determining the median.

The data reduction is preferably executed with a constant reduction. Further, alternative embodiments provide for the calibration quality moreover being able to be included in one or both of the above-described methods for data reduction. Thus, for example, as illustrated above, there may be a data reduction of the measurement signals of a measurement time period to one or a few representative measurement value pairs, wherein each measurement value pair for example comprises a measurement value and a time of the measurement. By way of example, a sub-minute based amount of measurement points can respectively be compressed to a value in the minute range.

Here, this representative measurement value pair may be stored alone, wherein, for example, the representative measurement value pair can comprise a representative measurement value or a representative measurement signal and a representative time of the measurement time period. However, for the purpose of keeping information, for example in order to carry out automatic fault avoidance (failsafe), additional information may be added to this representative measurement value pair. By way of example, use can be made of a 5-dimensional vector in which, for each representative time of the measurement time period, a mean and/or a standard deviation and/or a 25%-quantile and/or a 75%-quantile are also stored in addition to the median.

As an alternative to the plausibility analysis described in FIG. 2, in which slopes outside of the range specified by the thresholds 128, 130 are automatically rejected or discarded, or in addition thereto, provision can be made for further failsafe mechanisms. These can optionally be used in the calibration method and/or during the actual measurement for determining the analyte concentration from the measurement signals.

Figure 3:
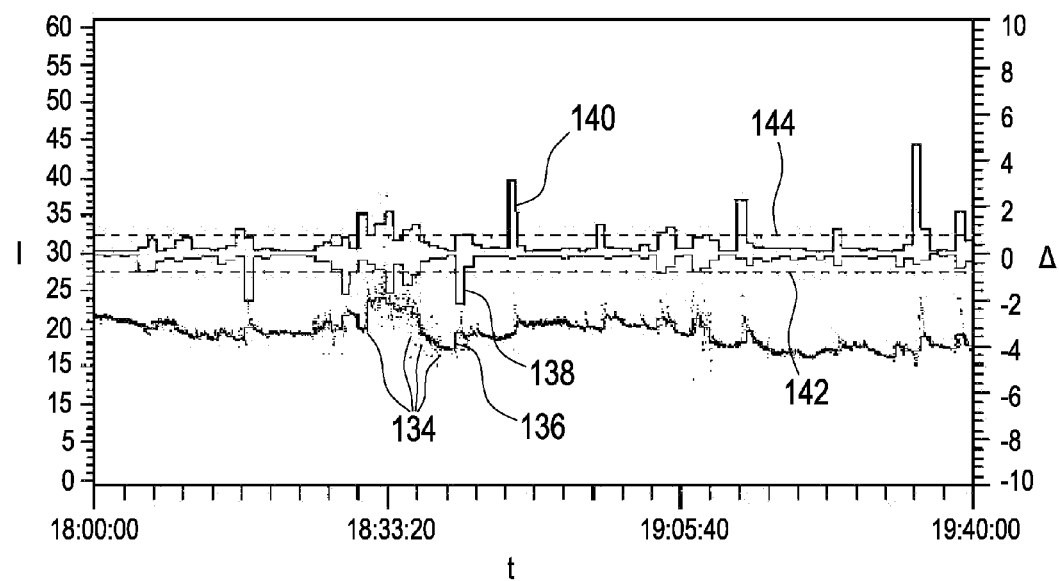
FIG. 3 shows a further exemplary embodiment of plausibility analysis using a failsafe mechanism.

FIG. 3 illustrates a measurement of raw measurement signals over a period of time. Here, the individual points denote the actual measurement signals. Here, the x-axis represents the time t. The measurement signals I are plotted on the left y-axis in arbitrary units. The measurement signals are denoted by reference sign 134 in FIG. 3. FIG. 3 furthermore in each case plots—this is denoted by reference sign 136—the median of the measurement signals 134 over one minute, which median is represented as a step function.

FIG. 3 furthermore illustrates two difference curves, which emerge from the differences between various quantiles and the median 136. These differences are specified on the right y-axis in arbitrary units. The difference between the 0.25-quantile and the median 136 (reference sign 138) and the difference between the 0.75-quantile and the median (reference sign 140) are shown. Within the scope of these teachings, a quantile of order p or a p-quantile generally specifies a value below which a prescribed proportion p of all cases of the distribution lies. Each value below $Q_p$ undershoots this prescribed proportion. Here p can be any real number between 0 and 1.

In order to obtain automatic fault avoidance, i.e., implement a failsafe method, these differences 138, 140 can be examined using a thresholding method. In the process, one or more thresholds 142, 144 can be prescribed, and the differences 138, 140 can be compared to these thresholds 142, 144. Accordingly, e.g., all differences 138 that lie below the lower threshold 142 can be discarded, as can all differences 140 that lie above the upper threshold 144. By way of example, this makes it possible to exclude, or provide very low weighting to, e.g., values in the minute range with particularly high deviations. By way of example, this makes it possible to implement an automatic failsafe method. However, care should preferably be taken in this case that the thresholds 142, 144 are not selected such that, e.g., values in the minute range are not spuriously removed during great changes, i.e., in the case of steep slopes, caused by changes in the analyte concentration.

A further aspect of the method according to this disclosure consists of the option of applying a calibration strategy. In principle, this calibration strategy can be used independently of the remaining aspects of the proposed method; however, it is particularly advantageous in combination with all or some of the above-described embodiments of the proposed method. Thus, a calibration strategy may for example consist of restricting the analyte concentration range, e.g., the glucose range, that can be seen by the user depending on the quality of the calibration. Thus, for example, outside of this range, a display can be switched to "lower boundary undershot" or "upper boundary overshot." Alternatively, or in addition thereto, the calibration strategy may also consist of inviting the user to a renewed calibration. As another alternative, or in addition to the above, the calibration strategy may also consist of signaling to the user when an expedient calibration time is present, i.e., an expedient time for carrying out the above-described calibration method and/or another calibration method. By way of example, an expedient calibration time may be present if there currently are low dynamics in the measurement signals and/or if an analyte concentration value to be expected deviates strongly from the previous values. Other types of expedient calibration times are also possible.

In a further aspect of this disclosure, it is possible to smooth raw values, for example by means of at least one exponential filter. By way of example, this smoothing can be used to carry out the calibration method and/or for the actual measurement in order to obtain smoothed measurement signals from the measurement signals. By way of example, use can be made of an exponential filter as described in, e.g., Hartung: Statistik. Lehr- and Handbuch der Angewandten Statistik [Statistics. Textbook and handbook of applied statistics], $14^{th}$ edition, Chapter XII, 1.3.4.: Exponentielles Glatten [Exponential smoothing], p. 672-673.

In order to smooth the raw values of the measurement signals, use can for example be made of a method in which $x_1, \ldots, x_m$ represent the values to be smoothed. Then the smoothed values $\tilde{x}_1; \ldots; \tilde{x}_m$ for example emerge from the following prescription:

$$\tilde{x}_1 = \begin{cases} x_1, & \text{if status } (x_1) = \text{valid,} \\ 0 & \text{otherwise.} \end{cases}$$

and $$\tilde{x}_{n+1} = \begin{cases} \alpha x_{n+1} + (1-\alpha)\tilde{x}_n, & \text{if status } (x_{n+1}) = \text{valid,} \\ \tilde{x}_n & \text{otherwise.} \end{cases} ;$$

$$n = 1, \ldots, m-1.$$

By way of example, the status of a value can be obtained by the above-described plausibility method. Thus, for example, the status can be set to invalid if one of the thresholds 142, 144 is respectively undershot or overshot in the plausibility method shown in FIG. 3. The status is otherwise set to valid. By contrast, the value $\alpha$ denotes a smoothing factor, lying in the interval between 0 and 1. By way of example, for $\alpha=0$ this constantly results in the initial value, whereas there is no smoothing for $\alpha=1$. The smoothing factor $\alpha$ can for example be set in a data storage device of the measuring equipment 110, for example in a persistent data storage device. As already illustrated above, the measuring equipment 110 can also have a decentralized design, and so a measurement system with a plurality of individual components, e.g., components connected by a unidirectional or bidirectional communication link, such as, e.g., continuously or discretely measuring sensors, control equipment, external storage devices or similar components can also be included by the term measuring equipment 110.

Furthermore, it is also possible to carry out at least one linearization step, both in the above-described calibration method and during the actual measurement for establishing the analyte concentration, or in merely one of the aforementioned method steps. By way of example, should it turn out that a current-analyte concentration relationship (or a corresponding ratio or function) is nonlinear (at least in sections), it is possible to carry out such a linearization step in an intermediate step. Here, e.g., the raw measurement signals, e.g., the raw current values, can be mapped by a linearization function such that the converted measurement signals have a linear relationship with the analyte concentration in the bodily fluid. This method lends itself particularly to a pre-calibration. By way of example, the corresponding conversion function can be determined batch-dependent at a measuring stand and can be stored in a data storage device of the control 114, e.g., once again in a persistent data storage device. The actual fine calibration can then be carried out in vivo, as described above.

Figure 4:
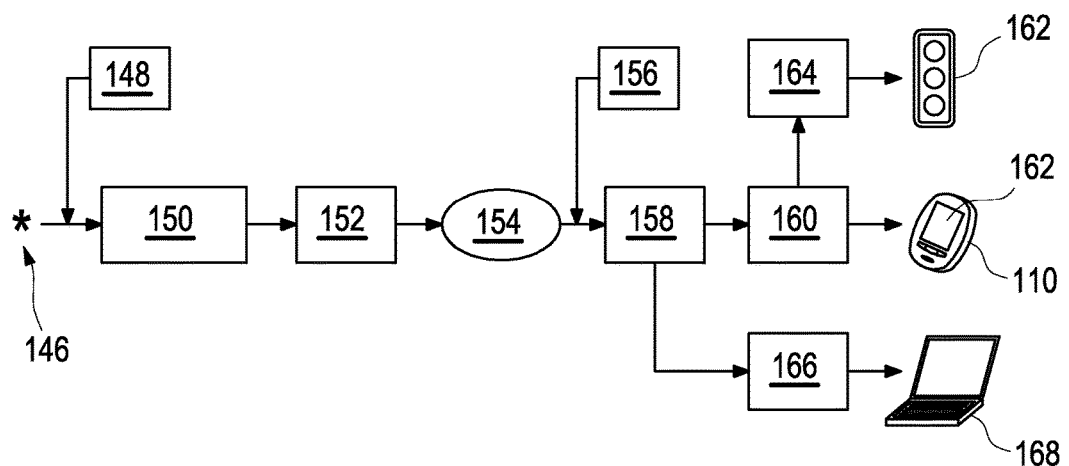
FIG. 4 shows a schematic flowchart of an exemplary embodiment of a method according to the invention.
Figure 5:
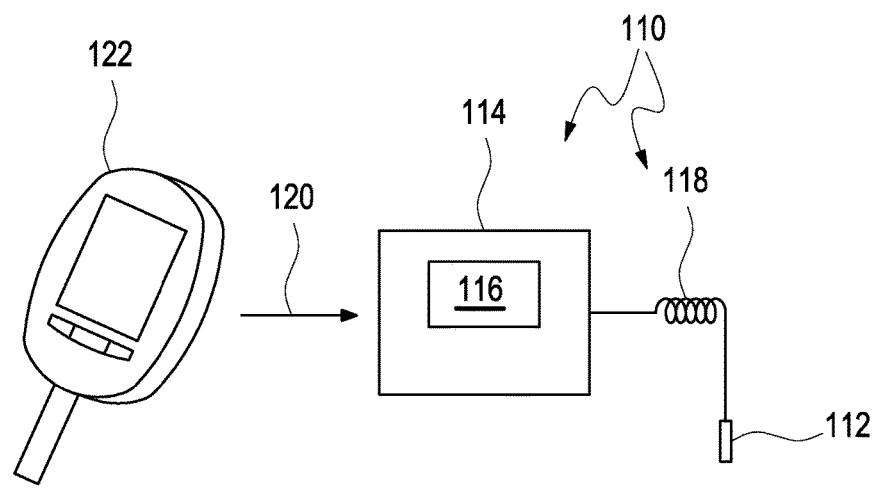
FIG. 5 shows an exemplary embodiment of measuring equipment according to the invention.

FIG. 4 finally illustrates a possible schematic flowchart of an exemplary embodiment of a method for operating measuring equipment 110 for detecting at least one analyte in a bodily fluid. Here, the reference sign 146 denotes the generation of one or more measurement signals, in particular as a function of time. By way of example, current measurement signals from the measuring equipment 110, more particularly from the blood glucose sensor 112, can be recorded every second. These measurement signals can optionally be smoothed; this is indicated by reference sign 148 and may include filtering. By way of example, use can be made here of an exponential filter, for example as per the above-described function.

In method step 150 there may optionally be data compression, for example as per one or more of the above-described methods. By way of example, this can a "downsizing" of measurement values recorded in the sub-minute range to values in the minute range.

Subsequently there may optionally be plausibility analysis in method step 152, in particular within the scope of a so-called failsafe method. In the process, as described above on the basis of FIG. 3 for example, implausible measurement signals may be discarded.

Subsequently, in method step 154, there can optionally be a transmission of the measurement signals processed thus. By way of example, there may be a transmission to the control 114 and/or a data storage device of the control 114 or a further-processing computational unit.

Subsequently there can be another optional smoothing in method step 156, for example there can once again be filtering.

Calibration points are formed in method step 158, in which reference values of associated reference measurements are assigned to corresponding measurement signals or the processed measurements signals (e.g., optionally smoothed and/or compressed measurement signals and/or measurement signals evaluated in any other way). This method step 158 can also be referred to as synchronization.

Subsequently, in method step 160, it is possible to carry out the calibration method for prospective calibration of the calibration points. As described above, for example, a relationship is produced in this calibration method between the measurement signals, i.e., optionally the processed measurement signals, and the analyte concentration in the bodily fluid. By way of example, as described above, this can be carried out by way of establishing the at least one probable slope and, optionally, the at least one probable axis intercept. This established relationship can subsequently be used for a measurement in, e.g., the measuring equipment 110 in order to determine the analyte concentration from the measurement signals. Said analyte concentration can for example be indicated on a display 162 of the measuring equipment 110.

As illustrated above, the method can optionally comprise a calibration strategy. By way of example, this calibration strategy may comprise a recommendation to carry out a calibration method. This is denoted by reference sign 164 in FIG. 4. By way of example, this recommendation can in turn be indicated on a display 162 of the measuring equipment 110. In particular, use can be made of a calibration strategy as described above on the basis of states (A)-(E).

While a relationship between the measurement signals and the analyte concentration is established for future measurements during the prospective calibration of the measuring equipment 110, there can optionally also be a retrospective calibration. This is denoted by reference sign 166 in FIG. 4. In the retrospective calibration, use can for example be made of calibration information added in the meantime in order to reevaluate older measurement signals, which additional calibration may have for example led to a more precise and less reliable calibration. By way of example, this may take place on the measuring equipment itself and/or, as illustrated in FIG. 4, on a further computer, e.g., a computer of a medical practitioner 168. This makes it subsequently possible to evaluate measurements with a greater accuracy.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

110 Measuring equipment for detecting an analyte in a bodily fluid
112 Continuously measuring blood glucose sensor
114 Control
116 Computer
118 Connection
120 Reception of reference values
122 Reference measuring equipment
126 Histogram of the slopes
128 Lower threshold
130 Upper threshold
132 Outlier
134 Measurement signals
136 Median of the measurement signals
138 Difference between 25th quantile and the median
140 Difference between 75th quantile and the median
142 Lower threshold
144 Upper threshold
146 Generating measurement signal
148 Smoothing
150 Data compression
152 Plausibility analysis
154 Transmission
156 Smoothing
158 Forming calibration points
160 Calibration method
162 Display
164 Recommendation to carry out the calibration method
166 Retrospective calibration
168 Computer of a medical practitioner

What is claimed is:

1. A method for operating measuring equipment for detecting at least one analyte in a bodily fluid, the measuring equipment including a continuously monitoring sensor and a reference measurement sensor, the method comprising:
   implanting the continuously monitoring sensor into the skin of a patient;
   detecting at least three calibration points, each calibration point comprising (i) a measurement signal obtained from the implanted sensor and corresponding to the concentration of the analyte in the bodily fluid and (ii) a reference value obtained using the reference measurement sensor, wherein the reference value corresponds to an actual present value of concentration of the analyte in the bodily fluid;
   establishing a plurality of possible slopes between the calibration points;
   using a robust estimation method to determine a probable slope from the plurality of possible slopes, the robust estimation method comprising a statistical estimation method which supplies stable statistical estimators even if outliers occur or if distribution assumptions are only approximately valid, the robust estimation being based on one or more permutation algorithms and/or on one or more sorting algorithms;
   determining through a plurality of the calibration points a plurality of straight lines having the probable slope; and
   using the continuously monitoring sensor to perform at least one measurement in which the probable slope is used with the measurement equipment to determine a concentration of the analyte in the bodily fluid.

2. The method of claim 1, further comprising:
   determining the axis intercepts of the straight lines;
   forming a median to determine a probable axis intercept from the axis intercepts; and
   using the probable axis intercept during the measurement.

3. The method of claim 2, wherein the calibration method is carried out repeatedly at different times, the method further comprising determining a new probable slope and a new probable axis intercept after the calibration method has been repeated and then using the new probable slope and the new probable axis intercept in at least one subsequent measurement.

4. The method of claim 1, further comprising preforming plausibility analysis during the calibration and using the plausibility analysis to discard unrealistic calibration points and/or unrealistic slopes and/or unrealistic axis intercepts.

5. The method of claim 1, further comprising using a sorting algorithm and/or a permutation algorithm during the robust estimation to form a median.

6. The method of claim 1, further comprising determining at least one current calibration quality having at least one confidence interval.

7. The method of claim 1, further comprising automatically inviting a user to carry out the calibration method.

8. The method of claim 1, wherein a user is invited to carry out the calibration method if at least one current measurement signal lies in a region in which the calibration method was not yet carried out with sufficient calibration quality.

9. The method of claim 1, further comprising informing a user if a current measurement signal lies in a region of insufficient calibration quality.

10. The method of claim 1, further comprising discarding at regular or irregular intervals calibration points that are older than a predetermined time threshold.

11. The method of claim 1, wherein the calibration points and/or the measurement signals are subjected to at least one smoothing method, using an exponential filter.

12. The method of claim 1, wherein the calibration points and/or the measurement signals are subjected to at least one linearization step, wherein the linearization step produces an approximately linear relationship between the measurement signals and the reference values.

13. The method of claim 1, further comprising detecting a plurality of the measurement signals from the measuring equipment over a measurement time period and applying a first data reduction method, comprising:
    combining the measurement signals with associated measurement times to form measurement value pairs, wherein a plurality of possible slopes are established between the measurement value pairs;
    using a median to establish a probable slope from the plurality of possible slopes, wherein a plurality of straight lines with the probable slope through the measurement value pairs are formed;
    selecting a representative time for the measurement time period and establishing functional values of the straight lines for the representative time;
    establishing a probable functional value from the functional values; and
    using the at least one probable functional value and the at least one representative time to replace the plurality of the measurement value pairs with a representative measurement value pair;
    the method further comprising applying a second data reduction method, comprising:
    forming a median and using the median to determine at least one probable measurement signal for the measurement time from the plurality of measurement signals, wherein the plurality of measurement signals are replaced by the probable measurement signal.

14. The method of claim 13, further comprising determining a standard deviation and/or a measure of the quantile.

15. The method of claim 13, further comprising comparing robust estimators of the measurement signals and parametric estimators of the measurement signals.

16. The method of claim 13, further comprising determining a trend from the plurality of measurement signals.

17. The method of claim 1, wherein, during the calibration method, a calibration of measurement signals from the measuring equipment is carried out against reference values of associated reference measurements and the calibration strategy comprises one or more of the following steps:
    a region of measurement signals from the measuring equipment that can be used for a measurement is restricted depending on a current calibration quality, wherein information is provided to a user when detecting measurement signals outside of the region that is usable or covered by calibration values or outside of a tolerance region based on the calibration values;
    a user is invited to carry out the calibration method again;
    a user is informed that now is a good time for carrying out the calibration method; and
    a user is invited to carry out the calibration method again at regular or irregular intervals or at predetermined times.

18. Measuring equipment for detecting at least one analyte in a bodily fluid, comprising:
    a continuously measuring bodily fluid analyte sensor adapted for implanting into the skin of a patient;
    a processor having a program stored in memory and configured for execution by the processor, the program including instructions for:
    detecting at least three calibration points, each calibration point comprising (i) a measurement signal obtained from the continuously measuring sensor implanted in a patient, the measurement signal corresponding to the concentration of the analyte in the bodily fluid and (ii) a reference value obtained using a reference measurement sensor, wherein the reference value corresponds to an actual present value of concentration of the analyte in the bodily fluid;
    establishing a plurality of possible slopes between the calibration points;
    using a robust estimation method to determine a probable slope from the plurality of possible slopes, the robust estimation method comprising a statistical estimation method which supplies stable statistical estimators even if outliers occur or if distribution assumptions are only approximately valid, the robust estimation being based on one or more permutation algorithms and/or on one or more sorting algorithms;
    determining through a plurality of the calibration points a plurality of straight lines having the probable slope; and
    using the implanted sensor to perform at least one measurement in which the probable slope is used with the measurement equipment to determine a concentration of the analyte in the bodily fluid.

19. The measuring equipment of claim 18, wherein the bodily fluid analyte sensor comprises a glucose sensor.

20. A method for operating measuring equipment for measuring concentration of an analyte in a bodily fluid, the measuring equipment including a continuously monitoring sensor, a reference measurement sensor, and a user interface, the method comprising:
    implanting the continuously monitoring sensor into the skin of a patient;
    initially calibrating the continuously monitoring sensor using measurement signals obtained from the implanted sensor that are matched to respective reference values obtained with the reference measurement sensor;
    using the calibrated sensor to continuously monitor the concentration of the analyte in the patient's bodily fluid;
    when a signal monitored from the calibrated sensor falls within a region that has less than a minimum number of calibration points, the user interface generates a visual, audible or haptic signal to the patient to recalibrate the continuously monitoring sensor; and recalibrating the sensor based on the visual, audible or haptic signal.

21. The method of claim 20, wherein the user interface invites the patient to recalibrate when the continuously monitoring sensor records a value that exceeds or falls below all previously recorded values.

22. The method of claim 20, wherein the user interface informs the patient that analyte measurement is terminated or interrupted and the continuously monitoring sensor suspends operation.

23. The method of claim 20, wherein the step of the user interface inviting the patient to recalibrate comprises producing a "must calibrate" signal.

24. The method of claim 20, wherein the step of the user interface inviting the patient to recalibrate comprises producing a "calibration recommended" signal.

25. The method of claim 20, wherein the step of the user interface inviting the patient to recalibrate comprises producing a "may calibrate" or "ready to calibrate" signal.

26. The method of claim 20, wherein:
the measuring equipment distinguishes between and selects one of the following states: (a) mandatory calibration, wherein a display of measurements is blocked until the measuring equipment is calibrated, and (b) recommended calibration, wherein the measuring equipment continues to display measurement results if the user does not calibrate; and
the user interface displays the selected state.

27. The method of claim 20, wherein the minimum number of calibration points is at least 3.

28. The method of claim 20, wherein the minimum number of calibration points is at least 2.

* * * * *